United States Patent
Raunio et al.

(10) Patent No.: US 9,816,977 B2
(45) Date of Patent: Nov. 14, 2017

(54) METHOD AND ARRANGEMENT FOR DETECTING FREE FIBRE ENDS IN PAPER

(71) Applicant: Kemira Oyj, Helsinki (FI)

(72) Inventors: Jukka-Pekka Raunio, Tampere (FI); Mikko Makinen, Espoo (FI); Henry Skoog, Roswell, GA (US); Clayton Campbell, Easton, MD (US)

(73) Assignee: KEMIRA OYJ, Helsinki (FI)

( * ) Notice: Subject to any disclaimer, the term of this patent is extended or adjusted under 35 U.S.C. 154(b) by 167 days.

(21) Appl. No.: 14/888,989

(22) PCT Filed: May 9, 2014

(86) PCT No.: PCT/FI2014/050344
§ 371 (c)(1),
(2) Date: Nov. 4, 2015

(87) PCT Pub. No.: WO2014/181044
PCT Pub. Date: Nov. 13, 2014

(65) Prior Publication Data
US 2016/0084819 A1    Mar. 24, 2016

(30) Foreign Application Priority Data
May 10, 2013 (FI) .................................. 20135483

(51) Int. Cl.
*G01N 21/86* (2006.01)
*G01N 33/34* (2006.01)
(Continued)

(52) U.S. Cl.
CPC ......... *G01N 33/346* (2013.01); *G01B 11/303* (2013.01); *G01N 21/4738* (2013.01);
(Continued)

(58) Field of Classification Search
CPC ........ G01N 33/346; G06T 2207/30124; G06T 2207/20224; G06T 2215/12; G06T 7/001
See application file for complete search history.

(56) References Cited

U.S. PATENT DOCUMENTS

| 4,300,981 A | 11/1981 | Carstens |
| 7,465,948 B2 | 12/2008 | Reich et al. |

(Continued)

FOREIGN PATENT DOCUMENTS

| WO | 9967625 A1 | 12/1999 |
| WO | 2009018445 A1 | 2/2009 |

OTHER PUBLICATIONS

Peter Hansson et al: "Topography and reflectance analysis of paper surfaces using a photometric stereo method", Optical Engineering, vol. 1 . 39, No. 9, Jan. 1, 2000 (Jan. 1, 2000), p. 2555, XP055030648, ISSN: 0091-3286, DOI: 10.1117/1.1287261 paragraph [04.1]-paragraph [04.2] figure 4.

(Continued)

*Primary Examiner* — Thanh Luu
(74) *Attorney, Agent, or Firm* — Thomas Horstemeyer, LLP (57) ABSTRACT

The invention relates to a method and arrangement for detecting free fiber ends in a paper surface. The method comprises illuminating a target sample (6) surface, which comprises free fiber ends, from at least two directions one at the time, with at least one light source (1). Original reflectance images are obtained for the target sample (6) surface with an imaging device (4), and a surface normal is estimated for each image pixel of the original reflectance image. Thus it is possible to reconstruct a reconstructed reflectance image from the estimated surface normals, and to compare the reconstructed reflectance image and the corresponding original reflectance image and to construct a difference (Continued)

image, where the differences represent shadow objects of the free fiber ends in a paper surface.

18 Claims, 4 Drawing Sheets

(51) Int. Cl.
    *G01N 21/47*       (2006.01)
    *G01N 21/89*       (2006.01)
    *G06T 7/00*         (2017.01)
    *G01B 11/30*       (2006.01)
    *G06T 7/41*         (2017.01)
    *G01N 21/892*      (2006.01)

(52) U.S. Cl.
    CPC ......... *G01N 21/86* (2013.01); *G01N 21/8914* (2013.01); *G06T 7/0004* (2013.01); *G06T 7/41* (2017.01); *G01N 2021/8663* (2013.01); *G01N 2021/8917* (2013.01); *G01N 2021/8924* (2013.01); *G06T 2207/30124* (2013.01)

(56) References Cited

U.S. PATENT DOCUMENTS

| | | | |
|---|---|---|---|
| 2007/0248246 A1* | 10/2007 | Cherkassky | ....... G01N 21/8983 |
| | | | 382/111 |
| 2008/0137101 A1 | 6/2008 | Spence et al. | |
| 2010/0040825 A1 | 2/2010 | Manifold et al. | |
| 2010/0155004 A1 | 6/2010 | Soerens et al. | |
| 2013/0116812 A1 | 5/2013 | Drasek et al. | |

OTHER PUBLICATIONS

Pawlak, J. J. et al. "Image analysis technique for the characterization of tissue softness". In Proceedings of Progress in Paper Physics Seminar, Graz, 2011, pp. 231-238, chapters 2-4; figs. 4-6.

Kuparinen, T. et al. "Paper surface topography using three-light photometric stereo". In Proceedings of IAPR Conference on Machine Vision Applications (MVA), 2007, pp. 45-48, chapters 2-5; fig. 1.

Finnish Patent and Registration Office Search Report for FI 20135483 dated Jan. 23, 2014.

International Search Report and Written Opinion for PCT/FI2014/050344 dated Aug. 1, 2014.

* cited by examiner

METHOD AND ARRANGEMENT FOR DETECTING FREE FIBRE ENDS IN PAPER

CROSS-REFERENCE TO RELATED APPLICATION

This application is the 35 U.S.C. §371 national stage application of PCT Application No. PCT/FI2014/050344, filed May 9, 2014, which claims priority to and the benefit of, FI Pat. Application No. 20135483, filed May 10, 2013, both of which are herein incorporated by reference in their entirety.

The invention relates to a method and an arrangement for detecting free fibre ends in paper according to the preambles of the enclosed independent claims.

TECHNICAL BACKGROUND

Tissue paper is the general name for toilet paper, paper towel, facial tissues, napkins and other soft paper products. Tissue paper is a sheet-like product manufactured continuously at speeds as high as 25 m/s. The width of the manufactured paper web in tissue paper machine can be up to 6 meter and the thickness of paper web is of the order of 50 µm. The tissue paper comprises random arrangement of wood fibres and smaller particles, such as minerals, and chemicals. Tissue products have promising future markets due to their sustainable raw material and lack of competing materials. Therefore it is expected that tissue manufacturing will continue to increase, which increases the financial significance of understanding the phenomena in tissue making process.

The most common type of tissue machine is the dry crepe machine in which the sheet is dried on one drying cylinder called a Yankee cylinder. This is because the strength of the low weight sheet is not sufficient to support sheet transfer between smaller drying cylinders. The tissue sheet is adhered to the Yankee cylinder and then detached from the surface with a blade. As a result a strong microstructure—crepe folds—is generated on the web. The detaching, known as creping, generates high softness and also compresses the web so that it can be transferred from the Yankee cylinder to the paper reel without a web break. The creping dominates the softness of tissue paper but the softness is affected significantly also by a combination of chemicals, softeners, added to the tissue sheet, the moisture content of sheet in creping process, and several factors in tissue machine operation.

Softness is one of the major properties in tissue paper. Although the tissue making process is quite well known, the final tissue product may not meet the required softness quality at the end-user. One reason for suboptimal quality control is the difficulty to measure softness of the tissue paper reliably. The tissue softness can be divided to bulk and surface softness. The bulk softness can be measured quite reliably by measuring the thickness and elasticity of sheet. However, the measurement of surface softness is not straightforward. Softness of tissue paper is usually studied with softness panel tests in which people evaluate subjectively softness of tissue paper. Furthermore, several measurement devices have been developed with the goal to correlate with rating by softness panels. However, the instrumental measurements conflict often with panel test results. This is partly because of the uncertainty of factors affecting to subjective softness feeling and partly because the current devices measure the forces, which are not in the same sensitivity scale as what the human perceives with.

One major shortcoming in current devices is that they do not detect the slight surface feeling of tissue. It has been suggested that the artificial robotic fingers studied in medical applications could be applied also in measurement of surface softness of tissue paper. However, the online application of such measurement device is not currently realistic. Pawlak et Elhammoumi [1] noticed that the high softness feeling correlates with the amount of fibres extending from the surface of tissue paper. Furthermore, an imaging based laboratory measurement device to measure the fibres from folded tissue paper was presented in the same article. However, the folding of paper requires additional devices and such measurement in on-line conditions at the paper machine would be rather impossible.

OBJECT AND SUMMARY OF THE INVENTION

An object of this invention is to minimise or even eliminate the disadvantages in the prior art.

An object is also to provide a method and an arrangement with which the amount of free fibre ends can be detected in paper, especially tissue paper.

A further object of this invention is to provide a method and an arrangement which are suitable for softness measurements of tissue paper on-line.

A further object of this invention is to provide a planar measurement method based on digital images which measures the amount of free fibres on the surface of paper, such as tissue paper.

These objects are attained with the invention having the characteristics presented below in the characterising parts of the independent claims.

Typical method according to the present invention for detecting free fibre ends in a paper surface, comprises
 illuminating a target sample surface, which comprises free fibre ends, from at least two directions one direction at a time, with at least one light source,
 obtaining for each light source direction an original reflectance image for the target sample surface with an imaging device,
 estimating a surface normal for each image pixel of the original reflectance image,
 reconstructing a reconstructed reflectance image from the estimated surface normals, and
 comparing the reconstructed reflectance image and the corresponding original reflectance image and constructing a difference image, where the differences represent shadow objects of the free fibre ends in a paper surface.

Typical arrangement according to the present invention for detecting free fibre ends in paper, especially in tissue paper grades, comprises
 an imaging device such as a digital systems camera, arranged to a distance from the sample holder, for obtaining original reflectance images of a target sample surface,
 at least two light sources, such as LED, attached around the imaging device, or one light source, which is attached to a supporting arm, which is arranged to rotate around the imaging device, the at least two light sources or the one light source being arranged to illuminate the target sample surface from at least two directions one direction at a time,
 a data processing unit, which is arranged
  to receive original reflectance images obtained for each light source direction from the imaging device, to estimate a surface normal for each image pixel of the original reflectance image, to reconstruct a reconstructed reflectance image from the estimated surface normals, and to compare the reconstructed reflectance image and the corresponding original reflectance image and to construct a difference image, where the differences represent shadow objects of the free fibre ends in a paper surface.

BRIEF DESCRIPTION OF FIGURES

FIG. 6a shows the close-up from the location of dark fibre at the middle of the image presented in the original reflectance image in FIG. 5a, FIG. 6b shows the close-up from the location of dark fibre at the middle of the image presented in the reconstructed reflectance image in FIG. 5b, FIG. 6c shows the close-up from the location of dark fibre at the middle of the image presented in the difference image in FIG. 5c.

DETAILED DESCRIPTION OF THE INVENTION

Typical method according to the present invention for detecting free fibre ends in a paper surface, comprises illuminating a target sample surface, which comprises free fibre ends, from at least two directions one direction at a time, with at least one light source, obtaining for each light source direction an original reflectance image for the target sample surface with an imaging device, estimating a surface normal for each image pixel of the original reflectance image, reconstructing a reconstructed reflectance image from the estimated surface normals, and comparing the reconstructed reflectance image and the corresponding original reflectance image and constructing a difference image, where the differences represent shadow objects of the free fibre ends in a paper surface.

Typical arrangement according to the present invention for detecting free fibre ends in paper, especially in tissue paper grades, comprises an imaging device such as a digital systems camera, arranged to a distance from the sample holder, for obtaining original reflectance images of a target sample surface, at least two light sources, such as LED, attached around the imaging device, or one light source, which is attached to a supporting arm, which is arranged to rotate around the imaging device, the at least two light sources or the one light source being arranged to illuminate the target sample surface from at least two directions one direction at a time, a data processing unit, which is arranged to receive original reflectance images obtained for each light source direction from the imaging device, to estimate a surface normal for each image pixel of the original reflectance image, to reconstruct a reconstructed reflectance image from the estimated surface normals, and to compare the reconstructed reflectance image and the corresponding original reflectance image and to construct a difference image, where the differences represent shadow objects of the free fibre ends in a paper surface.

Now it has been surprisingly found out that the existing problems can be solved by using the method and arrangement according to the present invention. In this application we introduce an imaging method which detects fibres extending from the surface of tissue paper based on the shadows of the fibres. A free fibre end produces a shadow to a certain location of a paper depending on the vertical and horizontal angle of illumination. These shadows are detected to estimate the density of free fibre ends in paper. The surface of tissue paper is rough and wavy because of the creping process and therefore the shadows of fibres cannot be detected as such from the reflectance images of tissue surface. The detection method according to the present invention utilises a photometric stereo method in which the target sample is illuminated from different angles and the surface normals of each image pixel are estimated. Furthermore, the Lambert's law is applied inversely to reconstruct the reflectance image from the estimated surface normals. Finally, the difference between the reconstructed reflectance image and the original reflectance image is compared and the shadows are detected from the difference image. The method presented in this application can be readily implemented on-line. The obtained softness results are comparable with results obtained by human softness panel tests. It has been noticed that the method detects the shadows and the behaviour mimics the results measured with a reference measurement system. The standard deviation in fibre counts in the imaging method is small indicating good repeatability of measurement.

According to one embodiment of the invention the target sample is a moving paper web, preferably a tissue web or the like, and that the method is performed on-line. The imaging method according to the present invention does not require any additional folding of paper and the images can be captured from the top of the moving paper surface. Thus by applying high-speed cameras and fast pulsing light sources the measurement arrangement can be used at on-line applications, for example at the running paper machine. On-line applications preferably utilize short exposure times, short light pulses and high accuracy alignment of images. According to one embodiment of the invention the number of shadow objects is counted and the process parameters are changed according to the obtained results.

According to one preferred embodiment of the invention a plurality of reconstructed reflectance images are reconstructed from the estimated surface normals, each of the reconstructed reflectance images are compared, separately, with the corresponding original reflectance image and difference images, where the differences represent shadow objects of the free fibre ends in a paper surface, are constructed. After that an average value of the number of the shadow objects in the difference images are calculated. In reconstruction of the two difference images are utilized the horizontal angles of illumination (0 and 180 degrees), which are perpendicular to the propagation of creping pattern of a tissue web. Use of two reflectance images improves the accuracy of the method by reducing the number of wrongly calculated shadow objects. When calculating the average value, the number of shadow objects in the two difference images are summed together and divided by two to get the average. The averaging also decreases the uncertainty because all shadow objects may not be real shadow objects but some other dark objects on the surface of sample.

The measurement arrangement according to the present invention comprises an imaging device, a light source and a data processing unit. The measurement arrangement may be, for example, a process device or a laboratory device which comprises a digital systems camera, a number of LEDs and a computer with a memory.

The imaging device may be any suitable high-resolution digital camera, such as high resolution CCD camera, for example digital system camera with 18 Mpix aps-c sensor. For on-line applications any suitable high-resolution, high-speed digital camera, such as high resolution CCD camera is preferred. The imaging device is arranged above the target sample, for example a moving tissue web, and arranged to take snapshots of the web. The geometric distortion and vignetting caused by the objective of the imaging device is typically so small that the calibration of the imaging device is not required.

The light source may be any suitable light source. A preferable light source is LED (light-emitting diode) because it is fast and economical light-source, especially for industrial on-line applications. For example, in on-line applications a number of light sources, which are LED flash lights, may be arranged around the imaging device, i.e. camera. The number of light sources may be at least four, preferably six, more preferably 12. The light sources flash one at the time and one original reflectance image is captured from the target sample during the each flash with the imaging device. This means that the number of images is the same than the number of light sources.

According to one embodiment of the invention the light source is a white LED. The white light includes photon particles of all possible wavelengths. The sensor of the imaging device comprises green, blue and red pixels which are sensitive for each colour, respectively. This means that green pixels of the sensor collect photons which wavelength correspond to green colour, blue pixels of the sensor collect photons which wavelength corresponds to blue colour and red pixels of the sensor collect photons which wavelength corresponds to red colour. In most of the colour digital imaging devices, such as colour digital cameras, the colour pixels are arranged to Bayer matrix shape. The sensor of the imaging device comprises group of 2×2 Bayer matrixes. Use of white light thus enables utilization of all colour pixels of the imaging device and of the Bayer matrix. In some embodiment it is also possible to use coloured light source, e.g blue LED.

An example of a suitable imaging device is Canon 550D camera with Sigma's macro 105 mm objective. In that case, the size of the image sensor is 5184×3456 pixels and each colour pixels from the 2×2 Bayer matrix (red, green, green and blue) is applied in the method because the colour of LED is white. The pixel values are represented with 14 bits. The size of the imaging area is 21×14 mm corresponding 4.1 μm×4.1 μm pixels.

The origin of the imaging arrangement is set at the centre point of the image on the surface of the target sample. The distance between the light source and the origin, as well as the distance between the imaging device and the origin of the imaging arrangement are preferably kept constant. The distance may be freely chosen depending on the application and process requirements.

Figure 1:
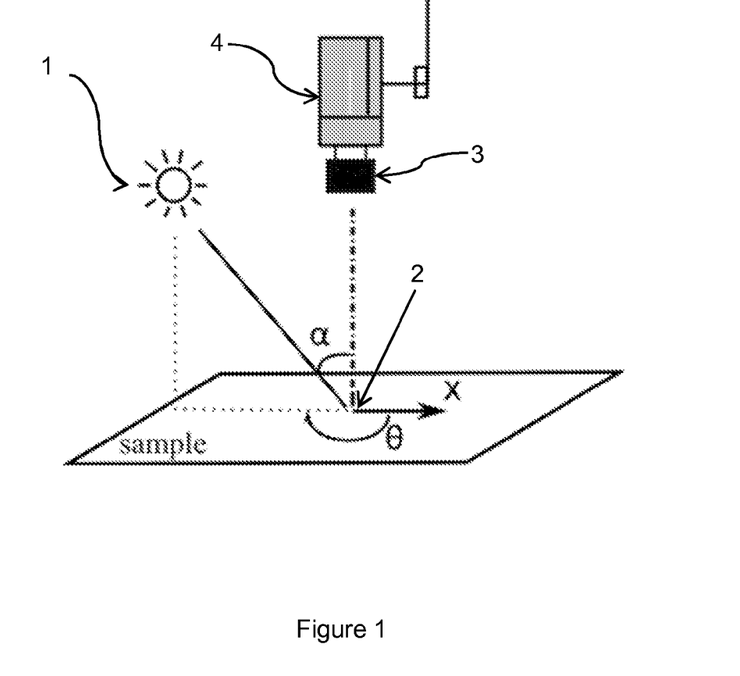
FIG. 1 shows an example of the imaging arrangement.

An example of the arrangement is shown in FIG. 1. The distance between the light source 1 and the origin 2 of the imaging arrangement may be, for example, 18.5 cm and the distance between the CCD sensor 3 of the imaging device 4 and the origin 2 may be 12 cm. The vertical angle a between the light source 1 and the surface normal is 30 degrees. The horizontal angle between the light source 1 and x-axis is marked with θ in FIG. 1.

Figure 2:
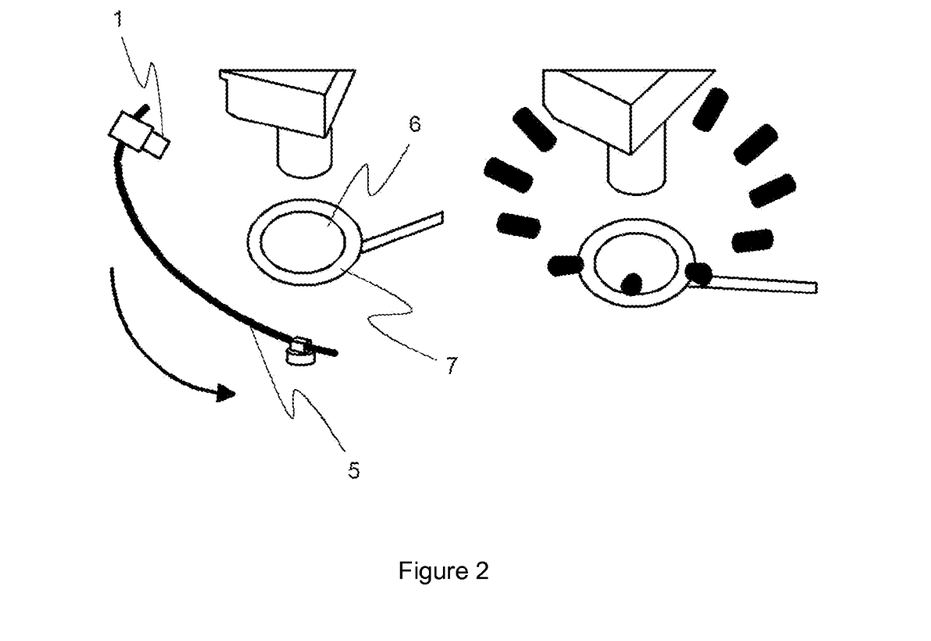
FIG. 2 shows another schematic drawing of the imaging arrangement.

Another example of the arrangement is shown in FIG. 2. The light source 1 is attached to a supporting arm 5, which rotates around the target sample 6. Thus the target sample 6 located on a sample holder 7 can be illuminated from various angles. For example, the sample 6 may be illuminated from 12 different horizontal angles indicating that the horizontal angle between the light source locations is 30 degrees (θ=0, 30, 60, 90, . . . , 330). The reflectance images are captured from each location. FIG. 2 shows a schematic drawing from the measurement device and measurement procedure according to one embodiment of the invention.

Figure 3:
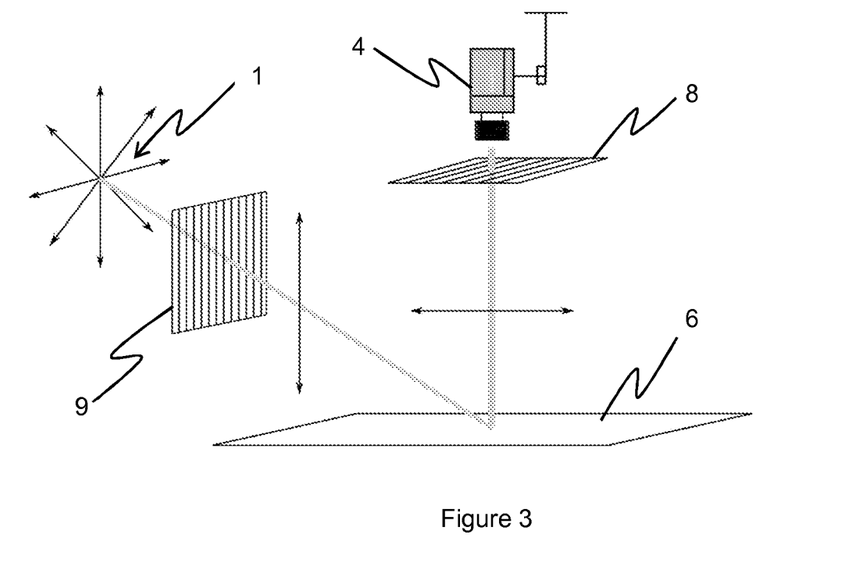
FIG. 3 shows an example of the imaging arrangement comprising polarizers.

According to one embodiment of the invention a first linear polarizer is arranged in front of the imaging device and a second linear polarizer is arranged in front of the light source, the first and the second linear polarizer being at 90 degrees angle in relation to each other, and the orientation between the polarizers is kept constant during the measurement. Generally, the surfaces can be divided roughly to specular and diffuse surfaces based on the reflection of the target. The photometric stereo method assumes that the reflection of the target is diffuse. The surface of paper is nearly diffuse. However, the wood fibres and mineral pigments in the paper may produce specular reflections and distort the estimation of surface normals. Therefore the unwanted effect of specular reflection may be reduced by crossing two linear polarizers at 90 degrees placed to the front of the light source, such as LED, and to the front of the object of the imaging device. The light which passes the first polarizer is blocked at the second polarizer if the light is specularly reflected. Both polarizers may be attached to supporting arms so the first polarizer in front of the object of the imaging device is rotating and thus the orientation between the polarizers is constant during the measurement. An example of the imaging arrangement comprising polarizers is shown in FIG. 3. The first linear polarizer 8 is arranged in front of the imaging device 4, and the second linear polarizer 9 is arranged in front of the light source 1. The polarizers 8, 9 are at 90 degrees angle in relation to each other. The polarizers 8, 9 block the light which is specularly reflected from the surface of the target sample 6. The arrows show the polarization of light.

According to one embodiment of the invention the beam pattern of the light source on the target sample surface is compensated by using a 2D second order polynomial fitted on the reflectance image. The shape of the beam pattern of the light source, such as LED, on the target sample surface depends mainly on the location and the beaming of the light source. The location of the light source is known in the arrangement according to the invention. However, the beaming includes uncertainties and therefore centre beam of the light source, such as LED, is not necessarily located in the middle of the target paper sample. The intensity of the light reflected from the target sample decreases in quadratic sense when the distance from the centre beam of the light source increases. Thus the beam pattern of the light source on the surface of target sample is compensated by a 2D second order polynomial fitted on the reflectance image. The 2D fitting problem can be defined in matrix form as follows $$[1 \ x \ y \ xy \ x^2 \ y^2][a \ b \ c \ d \ e \ f]^T = i \quad (1)$$

where x and y are the vectors containing the x and y coordinates of each pixel in the image. The vector i contains the intensity of the image pixels of the original image. The symbols from a to f are the coefficients of polynomial terms which are solved in the least squares sense. The polynomial is fitted to each Bayer matrix colour layer separately.

According to one embodiment of the invention the pixel intensity values are compensated by computing the distances between the each image pixel and the light source in order to obtain a matrix of pixel intensity compensation results, and multiplying the original reflectance image pointwise with the matrix of pixel intensity compensation results and dividing the original reflectance image pointwise with the 2D polynomial.

Figure 4:
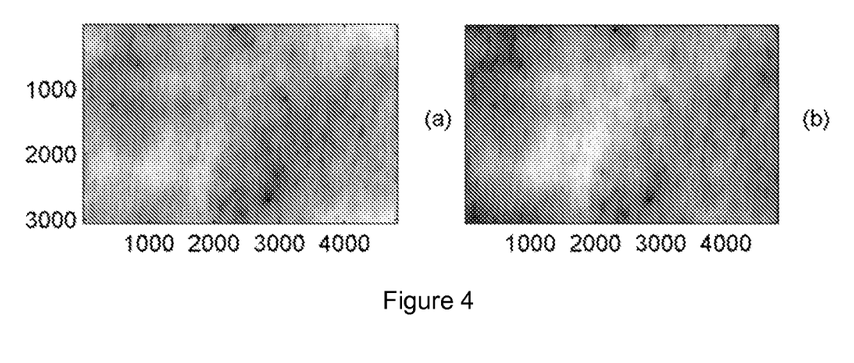
FIG. 4a shows the 3D surface of a tissue paper with the polynomial and cosSigma corrections.
FIG. 4b shows the 3D surface of a tissue paper without the polynomial and cosSigma corrections.

The present invention utilizes a so called photometric stereo theory, which is more closely described below. The computation of surface normals with photometric stereo is based on the brightness variation of the target sample surface. The photometric stereo theory assumes that the light arriving to the target sample surface is collimated. However, this is not necessarily the case in the present invention because normally the distance between the light source and the target sample is small and the physical size of the light source is small. Therefore, the orientation of the light beam arriving from the light source varies on the target sample surface. According to one preferred embodiment of the invention pixel intensity values are compensated by computing the distances between the each original image pixel and the light source in order to obtain a matrix of compensation results. The z location of the light source is divided with the distance as follows $$\cos\text{Sigma} = \frac{z_{light}}{\sqrt{\Sigma(x_{light} - x_{sample})^2}} \quad (2)$$

where $z_{light}$ is the z location of the light. The $x_{light}$ is the (x,y,z)-vector containing the coordinates of light source. The $X_{sample}$ is the (x,y,1)-vector containing the coordinates of the target sample. The compensation result is called cosSigma being the cosine of the vectors. After obtaining the matrix of compensation results, the original image is multiplied pointwise with the cosSigma-matrix, i.e. the matrix of compensation results, and divided pointwise with the 2D polynomial. An example of the effect of the corrections can be seen clearly from 3D surfaces shown in FIGS. 4a and 4b, where FIG. 4a shows the 3D surface of a tissue paper with the polynomial and cosSigma corrections and FIG. 4b shows the same 3D surface of a tissue paper without the polynomial and cosSigma corrections.

In photometric stereo two or more images are captured from a surface illuminated from different directions. Photometric stereo method estimates the surface normals of a Lambertian surface. The Lambertian (matt) surface is defined as one in which the reflected intensity is independent of the viewing direction. The Lambert's law represents the pixel intensity i at the point (x,y) as follows $$i = \rho EI_{3\times1}{}^T n_{3\times1} \quad (3)$$

where $\rho$ is the surface albedo describing the reflectivity of a surface, E is the intensity of a light source, n is the unit normal of the surface and I is the unit vector toward the light source. In the measurement setup $I^T$ is $$I^T = \begin{bmatrix} \cos(\theta)\sin(\alpha) \\ \sin(\theta)\sin(\alpha) \\ \cos(\alpha) \end{bmatrix} \quad (4)$$

where $\theta$ and $\alpha$ determine the orientation of the light source. The I vector is computed for each image pixel separately because the orientation of unit vector towards the light source depends on the location of pixel. The $\rho$En can be solved from the equation (3) because the imaging device detects and measures the pixel intensities (i) and the location of light source is known (I). However, the albedo depends on spatial location so the unit normal of the surface is not solved. Three light source directions are enough to determine the unit normal and the albedo from the equation (1), but the uncertainty of the estimate may be decreased by increasing the number of light source directions. According to one embodiment of the invention the target sample surface, which comprises free fibre ends, is illuminated from at least 6, preferably at least 8, more preferably at least 10, even more preferably at least 12, directions. Thus the number of light source directions is typically at least 6, preferably at least 8, more preferably at least 10, even more preferably at least 12. Then the Lambert's law can be represented in matrix form as follows $$i_{m\times1} = \rho E L_{m\times3} n_{3\times1} \quad (5)$$

where m is the number of light source directions, i is the intensity vector of the pixels for each light source direction, L is the matrix consisting of 1×3 unit vectors towarding each light source, and n is the unit normal of the surface. The problem is over determined for single pixel with number of light source directions and scaled unit normal m (scaled by the albedo) and can be solved by minimizing the square of error with pseudoinverse as $$\rho E n = m = (L^T L)^{-1} L^T i \quad (6)$$

The equation (6) is applied for each image pixel separately and this results scaled unit normal for each pixel.

The reflectance intensities of the target surface are reconstructed by using scaled unit normals and Lambert's law of the equation (5). The reflectance intensities are subtracted from the original reflectance intensities.

Figure 5:
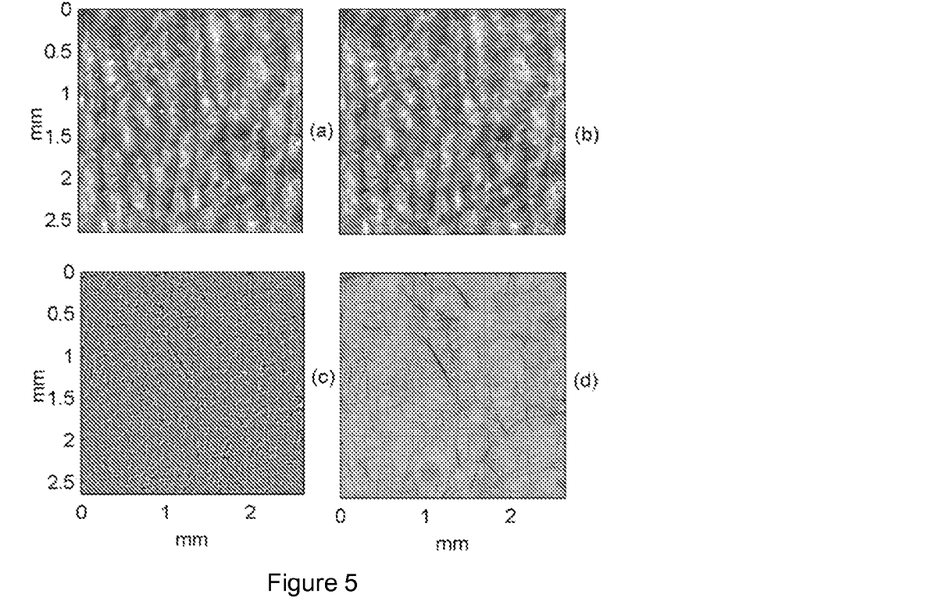
FIG. 5a shows a close-up from the original reflectance image.
FIG. 5b shows a close-up from the reconstructed image.
FIG. 5c shows a close-up from the difference image between the original and the reconstructed reflectance images.
FIG. 5d shows a close-up from the processed difference image O(x,y) which amplifies the shadows.
Figure 6:
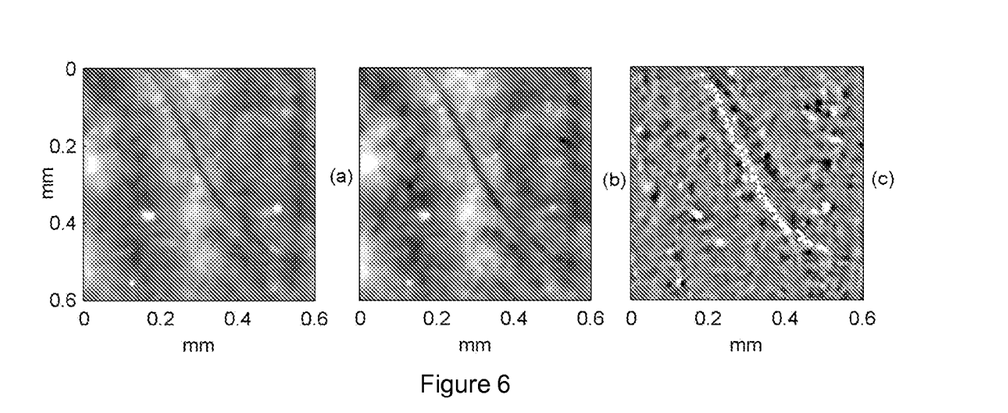

For example, FIG. 5a shows a small portion of the original reflectance image, FIG. 5b shows a reconstructed image from the same area computed with the method described above, and FIG. 5c shows the difference image between the original and the reconstructed reflectance images. The mean is removed from the images and the variance scaled to unity before the subtraction. The spatial variation larger than 0.3 mm is removed from the difference image with the linear 2D Bessel high-pass filter. It can be seen from FIG. 6a that the shadow caused by a fibre is extremely faint in the original reflectance image but the difference image of FIG. 6c reveals the shadow more clearly. The light source is illuminating the tissue paper sample from the direction of lower edge of the image) ($\theta$=90°). The maximum distance between the shadow and the fibre is 80 μm in y-direction) ($\theta$=−90° indicating that the difference of height between the fibre end and the tissue paper surface is)tan(60°) 80 μm≈140 μm. However, in most cases the fibre causing the shadow is invisible to camera or difficult to detect. Therefore only the number of free fibre ends on the surface is typically obtained with the method, neither the orientation nor the height.

Shadow objects of the free fibre ends are detected from the difference image. The shadow objects caused by the free fibre ends are seen as faint dark curves in the difference image. According to one embodiment of the invention the shadow objects are detected in the difference image by using filtering and/or processing methods which enforce the shadow objects of the free fibre ends in a paper surface. For example, the detection of shadow objects is based on line detection over the difference image. The line detection method applied is called orientated means in which the mean is computed for each pixel location and orientation of line. Such filtering/processing enforces the curves and lines caused by the shadows and in a resulting image the shadows can be seen as dark curves.

The shadows caused by the fibres can be seen as faint dark curves in the difference image. The detection of shadows is based on line detection in all orientations orientated over the image. The typical width of the wood fibres in paper is typically around 20 μm. The length of fibres in paper varies typically from 200 μm to 1000 μm. However, the length of the shadows varies depending on the angle and extension of free end of the fibre in paper sample surface being usually shorter than the length of the fibre. Therefore the width and the length of the objects detected from the image may be set to 16 μm and 100 μm, respectively. The line detection method applied is called orientated means in which the mean is computed for each pixel location and orientation of line. Let I(x, y) be a continuous function representing the image intensities given in a two-dimensional domain. The mean of object in orientation $\theta$ is denoted as follows $$F(x_0, y_0, L, W, \theta) = \qquad (7)$$
$$\frac{1}{WL}\int_{-W/2}^{W/2}\int_{-L/2}^{L/2} I(x_0 + x\cos\theta - y\sin\theta, y_0 + x\sin\theta + y\cos\theta)\,dy\,dx$$

where L is the length of the object and W is the width of the object. The mean is computed for several orientations of the object. The shadows are darker than the rest of the variation in paper and thus the minimum orientation value is selected for the resulting image. The minimum mean for several orientations can be denoted as follows $$O(x, y) = \min_{\theta \in [0,\pi]}(F(x, y, L, W, \overline{\theta})) \qquad (8)$$

where O(x,y) is the resulting processed difference image presented, for example in FIG. 5d. In that embodiment, the W and L are fixed to 16 μm and 100 μm respectively.

Figure 7:
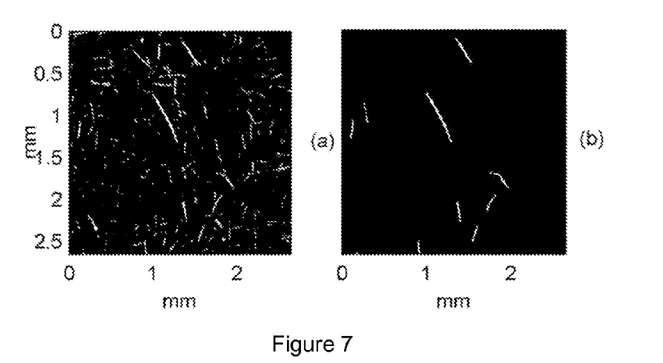
FIG. 7a shows the threshold binary image.
FIG. 7b shows the binary image from which the circular objects are removed.

According to one embodiment of the invention the shadow objects can be detected from O(x,y), i.e. the difference image, by thresholding. This comprises the steps of computing a histogram which shows the distribution of pixel values of the filtered/processed difference image in which the shadow objects are enforced, setting a threshold limit to a desired value and obtaining a thresholded difference image, removing circular objects from the thresholded difference image by using ellipse fitting algorithms, and accepting from the thresholded difference image shadow objects whose length is larger than an acceptance limit, and/or objects having eccentricity exceeding a predetermined value, and/or objects which major axis deviates at the most 30 degrees, 45 degrees or 90 degrees from the direction of the light source. The acceptance limit is, for example, based on the typical length of the wood fibre. The threshold limit is set to a desired value, for example to 0.2%. The threshold limit may be selected based on the fibre counts of the reference measurement system introduced below. An example of a threshold binary image, which is obtained, is shown in FIG. 7(a). From the threshold binary image only the objects whose length is larger than the threshold limit, e.g. 100 μm, are accepted. Furthermore, the shape of the accepted shadow object should be elongated. Therefore the length of the minor and major axis of ellipse fitted to the each object are calculated. The ellipse fitting algorithms are based on the 2D normal distribution fitted to the coordinate points. The covariance matrix ($\Sigma$) of the 2D normal distribution can be written in terms of the standard deviations a and a and correlation p between the x and y coordinates of object as follows $$\Sigma = \begin{bmatrix} \sigma_x^2 & \rho\sigma_x\sigma_y \\ \rho\sigma_x\sigma & \sigma_y^2 \end{bmatrix} \qquad (9)$$

The eccentricity of the corresponding ellipse is given by:

$$e = \left(\frac{2((\sigma_x^2 - \sigma_y^2)^2 + \rho^2\sigma_x^2\sigma_y^2)^{1/2}}{\sigma_x^2 + \sigma_y^2 + ((\sigma_x^2 - \sigma_y^2)^2 + \rho^2\sigma_x^2\sigma_y^2)^{1/2}}\right)^{1/2} \qquad (10)$$

In one embodiment of the invention the objects whose major axis is at least 5 times longer than their minor axis, i.e. the ones which have eccentricity larger than $2\sqrt{6}/5$ are accepted to final binary image, example of which is shown in FIG. 7b.

The objects detected from the final binary image may not be the shadows of fibres but for example colour variation on paper or unwanted reflection of minerals and fibres. Therefore, according to one preferred embodiment of the invention, only the shadows which deviate maximum 30 degrees from the direction of light source, i.e. the size of the cone is 60 degrees, are accepted. This means that the slope of the fibre which generates the shadow can be at most 18 degrees from the surface normal of the sample target if the angle between the slope and the direction of light source is 90 degrees. It is possible that the slope of the fibre is higher than 18 degrees meaning that the shadow is discarded from the count. However, if the fibre is illuminated from the direction which is opposite to the slope of the fibre the orientation of shadow is the same than the orientation of light source. Therefore, the fibre shadows are detected from the three locations which cover all possible orientations of shadows, i.e. 3×60 degree cone=180 degrees. The count of shadows from three images is summed and the result is the estimate of the density of the fibres. The cones are not overlapping because otherwise the same shadow could be counted twice which would distort the result.

According to an embodiment the method for detecting free fibre ends in a paper surface, comprises
  illuminating a target sample surface, which comprises free fibre ends, from at least four directions, with at least one light source,
  obtaining an original reflectance image for the target sample surface with an illuminating device,
  estimating a surface normal for each image pixel of the original reflectance image,
  reconstructing a reconstructed reflectance image from the estimated surface normals,
  comparing the reconstructed reflectance image and the original reflectance image and constructing a difference image, where the differences represent shadow objects of the free fibre ends in a paper surface.

According to an embodiment the arrangement for detecting free fibre ends in paper, especially in tissue paper grades, comprises
  an imaging device such as a digital systems camera, arranged to a distance from the sample holder, for detecting original reflectance image data,
  at least four light sources, such as LED, attached around the imaging device, or one light source, which is attached to a supporting arm, which is arranged to rotate around the imagining device,
  a data processing unit, which is arranged
    to receive original reflectance image data from the imaging device,
    to estimate a surface normal for each image pixel of the original reflectance image,
    to reconstruct a reconstructed reflectance image from the estimated surface normals, and
    to compare the reconstructed reflectance image and the original reflectance image and to construct a difference image, where the differences represent shadow objects of the free fibre ends in a paper surface.

EXPERIMENTAL

The performance of the imaging method presented in this application is evaluated with a reference measurement similar to the one introduced by Pawlak and Elhammoumi [1].

Figure 8:
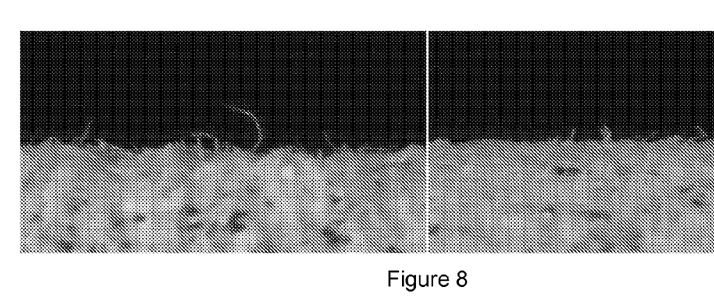
FIG. 8 shows two surfaces of folded tissue papers, the bath tissue on the left and kitchen towel on the right.
Figure 9:
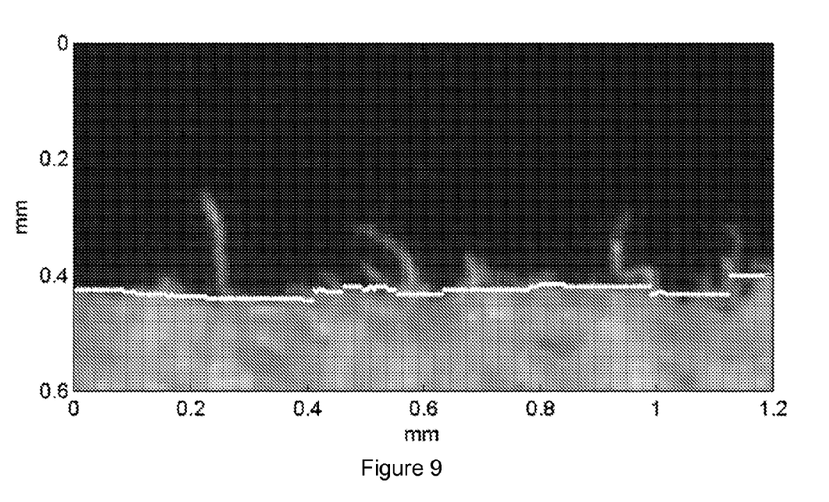
FIG. 9 shows a close-up from the folded tissue paper, the estimated surface boundary is drawn to image with white dots.

The tissue paper sample is folded over an edge and the image of the folded edge of the tissue paper is captured with a digital camera. FIG. 8 shows two surfaces of folded tissue papers, the bath tissue on the left and kitchen towel on the right. The width of the image is 6 mm (2×3 mm) and the height is 1.6 mm. The long fibres extending from the surface are seen clearly. The exact surface boundary in tissue paper sample is difficult to determine. Therefore only the free fibre ends which are extending from the assumed surface boundary of tissue paper by more than 100 µm are counted. The surface boundary is estimated by computing the difference of pixel vector in y-direction for each x location. The maximum difference in y-direction is obtained and the medium value from the neighbouring surface boundary points in x-direction is computed. FIG. 9 shows an example of the estimated surface boundary superimposed on the folded edge image. The fibres whose location is above the estimated surface boundary by more than 100 µm are considered as free fibre ends. The width of the folded edge is approximately 2 mm and this width is used to estimate the density of free fibre ends per area.

The alignment of fibres detected with the reference method described above and the shadows detected with imaging method according to the present invention is difficult because the estimation of exact location of fibres in the reference measurement method is uncertain. Therefore the density of free fibre ends of paper per area is computed and the results of the reference method and the imaging method are compared for three different tissue grades. Grade 1 is kitchen towel paper, Grade 2 is paper napkin and Grade 3 is bath tissue paper. The adjustable parameters in the imaging method according the invention are chosen to minimise the difference between the two independent measurements. The adjustable parameters are (1) the length of shadows considered to shadows of the free fibre ends, and (2) the threshold level in conversion from grey scale to binary image. The tissue samples are cut on the top of a machine reel so that the embossing, printing or other converting processes have not affected the structure of tissue samples. Densities of free fibre ends in each grade are measured at 36 locations with reference method and at 12 locations with the imaging method according to the invention. The fibres are counted from the side of tissue paper which has been in contact with the Yankee cylinder. The results are shown in Table 1.

TABLE 1

The averages and standard deviations of free fibre end densities estimated with the reference method at 36 measurement points per grade and the imaging system according to the invention at 12 measurement points per grade.

|  | Grade 1 | Grade 2 | Grade 3 |
| --- | --- | --- | --- |
| Average$_{ref}$ | 24.7 | 26.7 | 82.4 |
| Std.$_{ref}$ | 13.3 | 14.5 | 24.8 |
| Average.$_{img}$ | 36.3 | 40.1 | 64.5 |
| Std.$_{img}$ | 6.1 | 5.4 | 2.7 |

It can be seen from Table 1 that the results of the imaging method according to the invention follow the results of the reference method. For Grade 3 the amount of fibres is the highest whereas for Grades 2 and 1 the amount of fibres is significantly smaller than for Grade 3 and being smallest for Grade 1. The magnitudes of standard deviation are significantly smaller in the method according to the invention. The reason is the larger measurement area in the novel imaging method which decreases the uncertainty. Furthermore, the magnitude of standard deviation is smallest for Grade 3 which could be explained with the more stable tissue making process than in Grades 1 and 2. However, it can be seen that the fibre counts of the imaging method according to the invention differs from the results of reference method in each grade. The count difference could be explained with that the imaging method counts the shadows of fibres whose length is larger than 100 µm whereas the reference method counts the fibres having length from the surface boundary is larger than 100 µm. It is possible that the tilt angle between the paper surface and the fibres is so small that the reference method cannot detect such fibres although the shadow of fibre can be detected with the imaging method according to the invention.

The imaging analysis method according to the invention has two adjustable parameters: the length of the shadows considered as shadows caused by the free fibre ends, and the threshold level when converting from grey scale to binary image. The reference method is based on a rather crude approximation of the width of folded edge, 2 mm, and has the height of the fibre considered as free fibre ends as an adjustable parameter. Thus because of several uncertain parameters a perfect calibration of the novel imaging method based on the reference method is not possible.

REFERENCES

1. Pawlak, J. J., Elhammoumi, A.: Image Analysis Technique for the Characterization of Tissue Softness, In: International Paper Physics conference, Graz (2011)

The invention claimed is:

1. A method for detecting free fibre ends in a paper surface, the method comprising
    illuminating a target sample surface, which comprises free fibre ends, from at least two directions one direction at a time, with at least one light source,
    obtaining for each light source direction an original reflectance image for the target sample surface with an imaging device,
    estimating a surface normal for each image pixel of the original reflectance image,
    reconstructing a reconstructed reflectance image from the estimated surface normals, and
    comparing the reconstructed reflectance image and the corresponding original reflectance image and constructing a difference image, where the differences represent shadow objects of the free fibre ends in a paper surface.

2. The method according to claim 1, characterised in reconstructing a plurality of reconstructed reflectance images from the estimated surface normals,
    comparing each reconstructed reflectance image and the corresponding original reflectance image and constructing difference images, where the differences represent shadow objects of the free fibre ends in a paper surface, and
    calculating an average value of a number of the shadow objects in the difference images.

3. The method according to claim 1, characterised in that a unit normal of the surface for each image pixel is estimated by minimizing a square of error with pseudoinverse as $$n = \frac{(L^T L)^{-1} L^T i}{\rho E}$$

where n is the unit normal of the surface, $\rho$ is a surface albedo describing reflectivity of the surface, E is an intensity of a light source, L is a matrix consisting of 1×3 unit vectors toward each light source, and i is an intensity vector of an image pixel for each light source direction.

4. The method according to claim 3, characterised in that the reconstructed reflectance image is reconstructed by calculating a reflectance intensity for each image pixel from an equation $$i = \rho E L_{1 \times 3} n_{3 \times 1}.$$

5. The method according to claim 1, characterised in compensating a beam pattern of the light source on the target sample surface by using a 2D second order polynomial fitted on the original reflectance image.

6. The method according to claim 1, characterised in compensating pixel intensity values by computing distances between each image pixel and the light source in order to obtain a matrix of pixel intensity compensation results, and
    multiplying the original reflectance image pointwise with the matrix of pixel intensity compensation results and dividing the original reflectance image pointwise with a 2D polynomial.

7. The method according to claim 1, characterised in detecting the shadow objects in the difference image by using filtering and/or processing methods which enforce the shadow objects of the free fibre ends in a paper surface.

8. The method according to claim 7, characterised in computing a histogram which shows a distribution of pixel values of the filtered/processed difference image in which the shadow objects are enforced,
    setting a threshold limit to a desired value and obtaining a thresholded difference image,
    removing circular objects from the thresholded difference image by using ellipse fitting algorithms, and
    accepting from the thresholded difference image shadow objects whose length is larger than an acceptance limit, and/or objects having eccentricity exceeding a predetermined value, and/or objects which major axis deviates at the most 30 degrees, 45 degrees or 90 degrees from the direction of the light source.

9. The method according to claim 1, characterised in illuminating the target sample surface, which comprises free fibre ends from at least 6 directions.

10. The method according to claim 1, characterised in that the target sample is moving paper web and that the method is performed on-line.

11. The method according to claim 1, characterised in counting a number of shadow objects and changing process parameters according to an obtained result.

12. The method according to claim 1, characterised in arranging a first linear polarizer in front of the imaging device and a second linear polarizer in front of the light source, the first linear polarizer and the second linear polarizer being at 90 degrees angle in relation to each other, and
    keeping the orientation between the first linear polarizer and the second linear polarizer constant during a measurement.

13. The method according to claim 1, characterised in illuminating the target sample surface, which comprises free fibre ends from at least 8 directions.

14. The method according to claim 1, characterised in illuminating the target sample surface, which comprises free fibre ends from at least 10 directions.

15. The method according to claim 1, characterised in illuminating the target sample surface, which comprises free fibre ends from at least 12 directions.

16. An arrangement for detecting free fibre ends in paper, the arrangement comprising
    an imaging device such as a digital systems camera, arranged to a distance from a sample holder, for obtaining original reflectance images of a target sample surface,
    at least two light sources attached around the imaging device, or one light source, which is attached to a supporting arm, which is arranged to rotate around the imaging device, the at least two light sources or the one light source being arranged to illuminate the target sample surface from at least two directions one direction at a time, a data processing unit, which is arranged
   to receive original reflectance images obtained for each light source direction from the imaging device,
   to estimate a surface normal for each image pixel of the original reflectance image,
   to reconstruct a reconstructed reflectance image from the estimated surface normals, and
to compare the reconstructed reflectance image and the corresponding original reflectance image and to construct a difference image, where the differences represent shadow objects of the free fibre ends in a paper surface.

17. The arrangement according to claim 16, wherein the paper is a tissue paper grade.

18. The arrangement according to claim 16, wherein the at least two light sources are LED light sources.

* * * * *